United States Patent [19]
Lindow et al.

[11] Patent Number: 6,009,217
[45] Date of Patent: Dec. 28, 1999

[54] OPTICAL FIBER SENSOR FOR DISTINGUISHING BETWEEN THE PRESENCE OF LIQUID AND VAPOR PHASES OF A SUBSTANCE

[75] Inventors: James T. Lindow, Saratoga; Dean T. Mack, Los Altos; Edward R. McCourt, Jr., Palo Alto, all of Calif.

[73] Assignee: Mark Products, Inc., Sunnyvale, Calif.

[21] Appl. No.: 09/028,196

[22] Filed: Feb. 23, 1998

Related U.S. Application Data

[63] Continuation-in-part of application No. 08/760,400, Dec. 4, 1996, Pat. No. 5,757,988
[60] Provisional application No. 60/800,222, Dec. 5, 1995.

[51] Int. Cl.⁶ .................................................. G02B 6/00
[52] U.S. Cl. ...................................... 385/13; 250/227.16
[58] Field of Search ......................... 385/13; 250/227.16

[56] References Cited

U.S. PATENT DOCUMENTS

| | | |
|---|---|---|
| 4,590,462 | 5/1986 | Moorehead . |
| 4,596,443 | 6/1986 | Diemeer et al. . |
| 5,220,160 | 6/1993 | Sargoytchev . |
| 5,243,670 | 9/1993 | Bonicel . |
| 5,378,889 | 1/1995 | Lawrence . |
| 5,430,815 | 7/1995 | Shen et al. . |
| 5,757,988 | 5/1998 | Lindow et al. .......................... 385/13 |

FOREIGN PATENT DOCUMENTS 63-228105  9/1988  Japan .

*Primary Examiner*—Sara Crane
*Attorney, Agent, or Firm*—Robert S. Kelly

[57] ABSTRACT

An optical fiber sensor for inducing a microbend in an optical fiber in the presence of the liquid phase as distinguished from the vapor phase of a fluid such as water. The sensor includes a chamber with an expansible block located therein, and a thin band is provided about the block of a dimension and tensile strength such that any increase in outward expansive force in the block due to an increase in the presence of the fluid in its vapor phase only will not cause the band to rupture; however, when any liquid enters the chamber, the band will rupture to allow the block to expand in a particular direction to move a pusher bar which, in turn, moves a puller wire to bend the fiber at a location remote from the chamber.

19 Claims, 2 Drawing Sheets

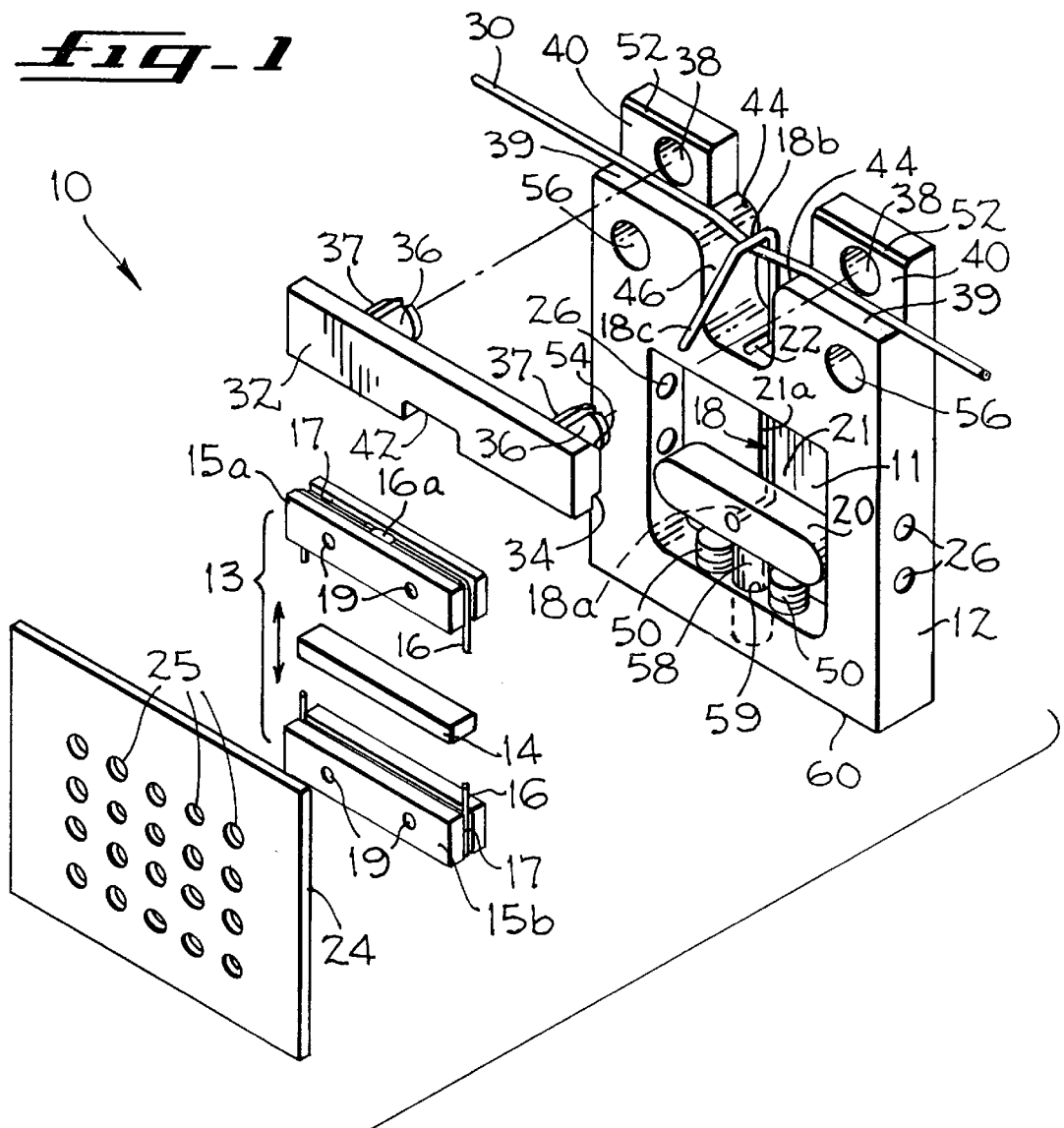
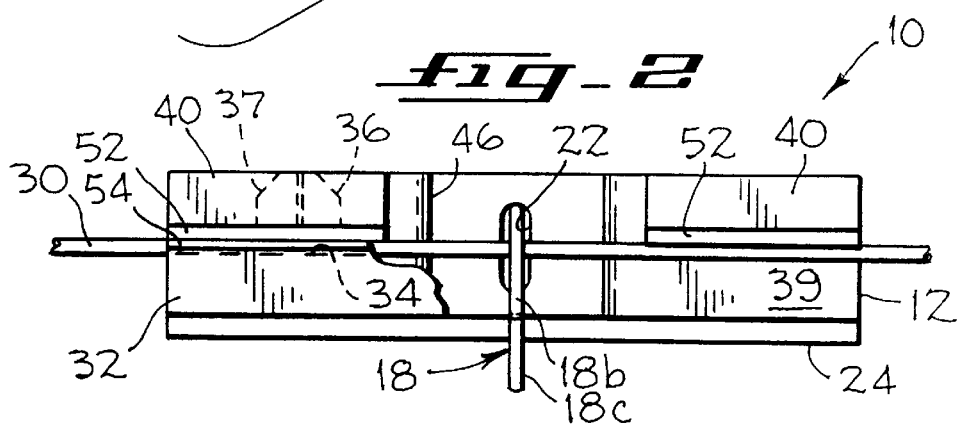

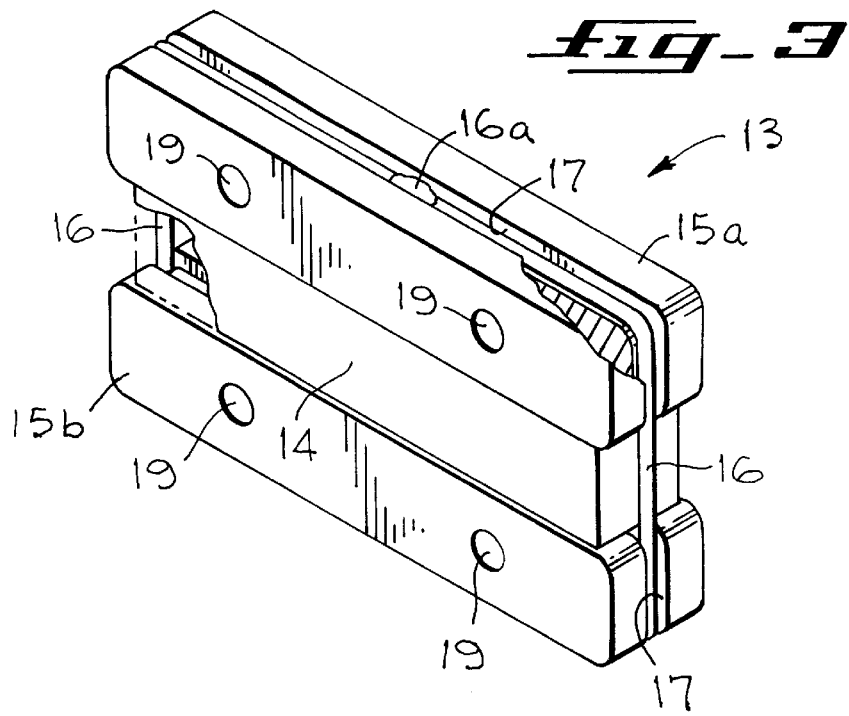
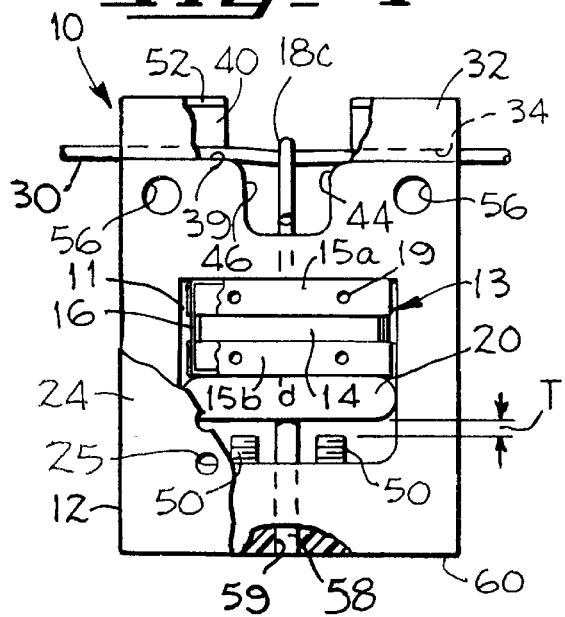
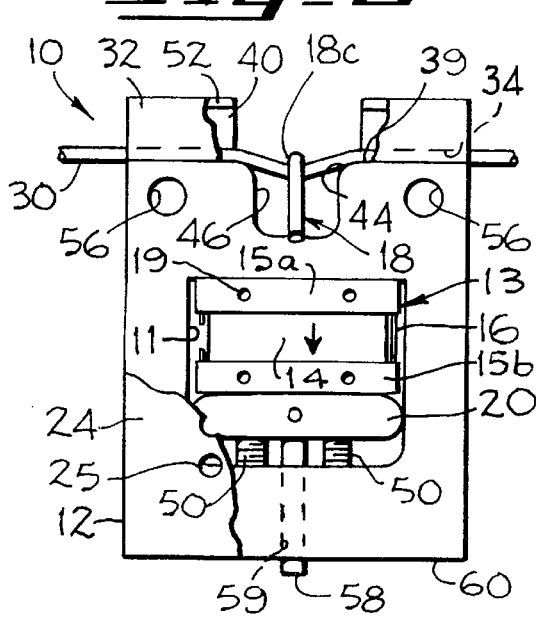

OPTICAL FIBER SENSOR FOR DISTINGUISHING BETWEEN THE PRESENCE OF LIQUID AND VAPOR PHASES OF A SUBSTANCE

CROSS-REFERENCE TO RELATED APPLICATIONS

This application is a continuation-in-part of U.S. application Ser. No. 08/760,400 filed on Dec. 4, 1996, by James T. Lindow et al, and entitled OPTICAL FIBER SENSOR UTILIZING A SWELLABLE DETECTOR MATERIAL, U.S. Pat. No. 5,757,988, such application claiming the benefit of U.S. Provisional Application No. 60/800,222, filed Dec. 5, 1995, and entitled OPTICAL FIBER SENSOR UTILIZING A SWELLABLE DETECTOR MATERIAL.

BACKGROUND OF THE INVENTION

1. Field of the Invention

The present invention pertains to optical fiber sensors for sensing fluid substances, such as water, and more particularly, it pertains to optical fiber sensors which utilize a swellable material in the presence of the fluid substance to be detected which swelling is arranged to mechanically cause a microbending in the optical fiber that can readily be detected and analyzed by conventional monitoring devices.

2. Description of the Prior Art

Optical fiber sensors for sensing the presence of a particular fluid substance such as water vapor, water, petrochemicals, etc., are well-known in the prior art. The presence of the fluid substance at a remote location, such as a buried telecommunications box, is sensed by a carefully chosen substance which is caused to thereby swell and mechanically create a stress in or, particularly, a microbending in the optical fiber which condition can then be readily detected by the attenuation in the signal transmitted by the fiber or by optical time domain reflectometer (OTDR) circuitry which reacts to the signal loss at the microbend and accurately pinpoints its location along the length of the optical fiber.

Prior United States patents which disclose the use of a fluid sensor employing the microbending of an optical fiber include the Pat. No. 5,243,670 to Bonicel wherein the presence of moisture is detected within a closed chamber; U.S. Pat. No. 4,596,443 to Diemeer et al disclosing a fiberoptic sensor for detecting the presence of a liquid such as ground water within a multiconductor cable; U.S. Pat. No. 5,378,889 to Lawrence disclosing a fiberoptic sensor for the detection of hydrocarbon fuels; and U.S. Pat. No. 5,430,815 to Shen et al which discloses an optical fiber sensor for detecting the presence of water wherein a swellable material forces the optical fiber to be bent about a curved mandrel. Optical fiber sensors utilizing the microbending of the fiber for detection purposes have also been used to detect shockwaves as shown, for example, in the prior patent to Sargoytchev, U.S. Pat. No. 5,220,160.

While in the foregoing patents the swellable material directly impacts upon the fiberoptic cable, the location for detecting the presence of particular fluid substance may be separated from the location of the fiber attenuation imparting means so as to prevent any contact therebetween with a mechanical connection being provided to impart a bending to the fiber upon the remote sensing of the fluid substance as shown, for example, in the U.S. Pat. No. 4,590,462 to Moorehead disclosing an optical fiber sensor for the detection of hydrocarbons.

A particular industry which has utilized optical fiber sensors in the past is the telecommunications industry wherein fiberoptic splice cases are used at remote locations as junctions or splice points for the fiberoptic cables. Typically, these splice cases are buried underground and are thereby subject to water intrusion, for example, as a result of physical damage, improper sealing or direct leakage through a cut in the cable sheath. Since such water instrusion can damage the optical fibers and the cladding thereof and can therefore have significant consequences on the accuracy and reliability of the information communicated over the fiberoptic cables, it is imperative that the presence of water in the splice case be communicated to some remote operating point as soon as possible.

A particular problem with prior art optical fiber sensors in dealing with the presence of water in splice cases is the lack of discrimination in the sensor in distinguishing between free water (which can produce the adverse consequences as pointed above) and water vapor (which will unavoidably occur and which is generally much less harmful). It is understandable that a high humidity can build up in objects like buried splice cases over time particularly during the wet seasons. If the cumulative effects of the continued presence of a highly humid atmosphere causes the sensor to be triggered even though no free water is present, unnecessary and costly replacements or repairs may occur.

SUMMARY OF THE INVENTION

In accordance with the present invention an optical fiber sensor is provided which utilizes the well-known technique of providing a block of swellable or expansible material which expands in the presence of a particular liquid, such as water, and which expansion causes a microbending of an optical fiber which can be sensed at a remote location, for example, by typical OTDR equipment.

With the present invention, a chamber is provided for the block of expansible material and a mechanical connection is made between the block and the optical fiber so that expansion of the material in a particular direction results in bending of the fiber. In order to prevent the expansible material from bending the fiber solely in the presence of the vapor phase of the liquid, e.g., water vapor, a restraint, e.g., a thin, non-extensible band, is placed securely about the block of expansible material so that expansion of the block in the particular direction to bend the fiber is prevented during the vapor phase of the liquid. However, the presence of free liquid in the chamber which can be absorbed by the block of expansible material creates an expansive force in the block to overcome the restraint, i.e., break the thin band, and permit the expansive movement of the block to bend the optical fiber.

In a preferred embodiment of the invention the optical fiber is spaced from the chamber and out of direct contact with the expansible material. A mechanical member connects the expanding block of material with the optical fiber so as to translate expansive movement of the block in the particular direction into a corresponding bending of the fiber.

In a further preferred embodiment of the invention, the fiber is arranged to be deflected into a cavity when the expansible material is caused to swell to move the mechanical member whereby three fiber support surfaces of controlled geometry are provided at the microbend, such support surfaces including the mechanical member pushing the fiber into the cavity as well as the two spaced support surfaces for the fiber at the edges of the cavity. In this arrangement, the fiber deflection will be precisely predetermined under a given degree of expansion of the swellable member so that the light loss provided by the microbending of the fiber can be readily and correctly analyzed and processed.

BRIEF DESCRIPTION OF THE DRAWINGS

FIG. 1 is an exploded view of the optical fiber sensor of the present invention.

FIG. 2 is an enlarged top plan view of the assembled optical fiber sensor of FIG. 1 with a portion thereof being broken away for the purpose of illustration.

FIG. 3 is an enlarged isometric view of the expansible material block and restrictive band assembly of the optical fiber assembly of FIG. 1.

FIG. 4 is a front elevation of the optical fiber sensor of FIG. 1 with portions thereof being broken away and particularly illustrating the device in the absence of the detectable liquid.

FIG. 5 is a front elevation of the optical fiber sensor of FIG. 1 similar to FIG. 4 but illustrating the condition of the sensor upon the intrusion of the detectable liquid into the sensor chamber and the resultant microbending of the optical fiber.

DESCRIPTION OF THE PREFERRED EMBODIMENT

The components of the optical fiber sensor 10 of the present invention are shown in exploded form in FIG. 1. The sensor is designed to utilize the well-known phenomenon of measurable transmitted light loss from a selectively bent optical fiber 30 to indicate the presence of a particular fluid substance. The fluid to be detected may be one which has both a liquid phase and a vapor phase, e.g., water. In order to provide for the basic detection process, a swellable or expansible member 13 is provided, which member is adapted to predictably swell in one of its dimensions (the vertical direction in the FIG. 1 embodiment as indicated by the arrows) in the presence of the liquid and which swelling is designed to cause the bending of the fiber 30 in a controlled manner to provide the appropriate light loss signal to conventional monitoring equipment such as an OTDR (not shown) operating from a distant location along the length of the fiber.

While the optical sensor 10 of the present invention may thus be used for detecting various types of liquids in various types of environments, in the embodiment of the invention specifically disclosed herein, the sensor 10 is particularly intended to be utilized in connection with the detection of free standing water and to distinguish such water from water vapor alone in a manner to be explained presently. Such water detection is particularly useful, for example, in the monitoring of telecommunications fiber optic splice cases conventionally used in the telecommunications industry at locations such as junctions or splice points for fiber optic cables. Typically, the splice cases are buried underground and are thereby subject to water and/or water vapor intrusion if, for any reason, the case seals should fail or the case should be cut or otherwise damaged. Since water leakage into the cases can cause damage to the fiber, cable assembly and splices and can therefore have significant consequences on the accuracy and reliability of the information communicated over the fiber cables, it is imperative that the presence of water in the splice case be communicated to some remote operating point as soon as possible. The sensor of the present invention is designed to accomplish that function.

The expansible member 13 is shown in exploded form in FIG. 1 and in its normal (unactivated) assembled form in FIG. 3. The member 13 will be seen to be comprised of block 14 of swellable material which is sandwiched between a pair of end members 15a and 15b with the end members and block 14 being secured together by a thin metallic wire or band 16 that extends wholly about the outer periphery of the assembly within a groove 17 in the outer peripheral surfaces of the end members. The free ends of band 16 are secured together (in a manner to be explained in greater detail hereinafter) atop the end member 15a by a drop of adhesive 16a so that the band is tightly secured about the assembly but without any significant additional tension (i.e., less than about one-tenth of an ounce) being imposed thereon. A pair of holes 19 are drilled through each of the end members 15a, 15b for a purpose to be explained hereinafter.

In choosing the particular material for the swellable block 14, a suitable inert hydrophilic material should be used which will swell substantially and reliably in the presence of free water, as for example, a polyvinyl fluoride or a polymer such as a crosslinked polyvinyl alcohol or other polymers as discussed in prior U.S. Pat. No. 5,015,843 to Sietz et al. In accordance with the present invention, however, the material chosen is a small cell size, pre-compressed cellulose sponge with the pre-compression of the sponge being such that expansion due to the presence of water will occur in the direction of the arrows (FIG. 1). Thus, the swelling expansion of the sponge block 14 occurs in the vertical direction (as seen in FIG. 1).

It is an important feature of the present invention that the wire or band 16 have enough tensile strength so that any increase in humidity (water vapor) alone will not create enough expansive pressure in the block 14 to break the band and cause the member 13 to expand (in the direction of the arrows, FIG. 1). In order to insure that this will be the case, the average tested tensile strength of the wire 16 should be at least twice the strength necessary to resist the internal pressure from the expansible block 14 under maximum water vapor (100% humidity) conditions. However, the pre-compression of the block 14 must be enough such that the introduction of free water thereto creates an expansive force which readily causes the wire 16 to break. For this purpose we have chosen for band 16 a platinum wire of about 1 mil in diameter and for the swellable block 14 a sponge which when expanded has a thickness at least several times the initial compressed thickness.

In preparing the expansible member 13 for use in the sensor of the present invention, the end members 15a, 15b are first placed in a mandrel comprised of a series of spaced pins (not shown) which are adapted to be received in the holes 19 so as to space the end members apart slightly as shown in FIG. 3. The sponge block 14 is then fitted between the end members and wetted thoroughly so that it will expand into tight contact with the end members. The wire 16 is then wrapped securely about the assembly along groove 17 without applying any significant tensile stress in the wire until it is overlapped along the upper face of end member 15a where a drop 16a of a quick-drying glue is applied and the continuing end of the wire 16 is cut off. While the assembly remains captured by the mandrel pegs, it is thoroughly dried out so that the block 14 retains its shape but without exerting any significant pressure on the enclosing band 16. The expansible assembly 13 can then be removed from the mandrel pegs and will be ready to be used in the sensor 10 of the present invention.

As can be seen from FIG. 1, the sensor 10 is comprised of a generally rectangularly shaped, recessed body member 12 provided with a rectangular cavity 11 therein in which is adapted to be closely fitted at the upper end thereof the expansible assembly 13. The top of the expansible assembly 13 is positioned, as seen in FIG. 3, in engagement with the upper end of the cavity 11, and a pusher bar 20 of a rigid material is positioned in contact with the lowermost end member 15b of the expansible assembly 13 so that the pusher bar 20 will move downwardly therewith when the presence of water in cavity 11 causes the band 16 to break and the assembly 13 to expand. A puller wire 18 is inserted into and securely attached to the pusher bar 20 at its lower end 18a thereof and is arranged to slide along a groove 21a in the flat rear wall 21 of cavity 11 when the pusher bar 20 is moved. The upper end of the puller wire 18 passes through a slot 22 at the upper end of body member 12 to a position outside of the cavity 11 and above the fiber 30. The upper end of the puller wire 18 is formed with a right angle section 18b which lies above and in contact with the fiber 30 and a forwardly and downwardly bent section 18c serving to enclose the fiber. It will therefore be seen that as the pusher bar 20 is lowered under the impetus of the expanding assembly 13, the puller wire 18 will act through section 18b thereof to pull downwardly on the fiber causing it to bend and creating the detectable light loss and/or reflection in the fiber for the conventional monitoring devices such as the OTDR previously mentioned.

The expansible assembly 13 and the pusher bar 20 are both captured within the body cavity 11 by means of a cover plate 24 which is adapted to be bonded or otherwise securely fastened to the peripheral face of the body member 12 above the cavity 11 thereof. The cover plate 24 is provided with a plurality of holes 25 therethrough to allow free inflow of water to the various surfaces of the sweller block 14 within expansible assembly 13. As can be seen in FIG. 1, each of the side walls of the body member 12 is provided with a plurality of apertures 26 leading into the cavity 11 to further provide for the free flow of water into the cavity and to the sweller block 14. Thus any water that is present about the sensor will be allowed to flow freely into the cavity 11 and about the sweller block 14 thereby causing its expansion in its transverse dimension, i.e., downwardly toward the open end of the cavity.

In order to permit the fiber 30 to be readily attached to (or detached from) the optical fiber sensor 10 of the present invention, a removable capture block 32 (FIG. 1) is provided. The capture block is formed of a generally rectangular shape and includes two spaced pairs of flexible projections 36, 37 which are adapted to be pressed into cylindrical apertures 38 in a pair of spaced and upwardly projecting flanges 40 at the upper end of the body member 12. A notch 34 (FIG. 1) is provided along the lower and inner face of the capture block so as to provide a passage just large enough for the capture of the fiber 30 along a pair of flat ledges 39 formed at the upper end of body member 12. Thus, with the capture block removed from the body, as shown in the exploded view of FIG. 1, the fiber may be slipped under the end 18c of the puller wire 18 so as to rest on the ledges 39 up against flanges 40. The projections 36, 37 of capture block 32 are then pressed into the apertures 38 with the notch 34 therein securing the fiber and preventing its lateral movement but permitting free longitudinal movement thereof when it is pulled by puller wire 18 and thus providing a rapidly removable and replaceable snap-fit connection. It will be seen, therefore, that the optical fiber 30 can be removed and replaced in the sensor 10 without requiring the threading of an end of the fiber through the body of the sensor. As can further be seen in FIG. 1, the bottom of the capture block is provided with a notch 42 to permit the projection of and free movement of the enclosing end 18c of the puller wire.

In the embodiment of the invention shown, controlled geometry is used in the sensor to precisely define the manner in which the optical fiber 30 is bent from its initial position (no water or other detectable liquid present) to a final (maximum allowable) position limiting the microbending of the fiber so that permanent damage thereto does not occur. For this latter purpose, it will be noted that a pair of set screws are adjustably threaded into the bottom wall of the body member 12 forming the bottom of the cavity 13, and, as particularly seen in FIGS. 4 and 5, such set screws are designed to abut against the bottom of the pusher bar 20 after the sweller block 14 has expanded by a maximum distance T. Obviously, such distance T can be adjusted for different operating conditions by raising or lowering the screws 50 within the body member 12.

An aspect of the controlled geometry feature is to relatively tightly enclose the fiber 30 by means of the notch 34 as aforedescribed but yet permit free sliding longitudinal travel of the fiber as it is pulled along the ledges 39 during the bending operation as shown by the fiber movement, as indicated, between FIGS. 4 and 5. As the fiber is bent downwardly, the fiber is pulled over the ledges 39 around a pair of surfaces 44 curved about a uniform radius and into a cavity 46 in the body member. The smoothly curved shape of the surfaces 44 is designed to minimize the reflective losses and to produce splice-like microbending losses in the fiber without damaging or permanently altering the optical transmission characteristics of the fiber. The size of the puller wire 18 is also carefully chosen so as not to create undue stress at its contact surface with the fiber in the section 18b of the puller wire. In the present instance, utilizing a conventional single mode telephone communication fiber with a common size of 125/9 (about 250 microns in diameter including the buffer layer thereof) a size of puller wire of 0.014 inches in diameter was chosen. The smooth corners 44 about which the fiber is bent are arcs with a radius of about 0.0625 inches. With this three support surface (44-18b-44) geometrical arrangement for the fiber at the deflection cavity 46, the sensor 10 of the present invention can be used to produce signal losses in the fiber 30 from about 0.05 db to about 2.5 db at the typical telecommunications wavelengths of from about 1300 nanometers to about 1650 nanometers and with the maximum fiber deflection distance T (FIG. 3) being from about 20 mils to about 50 mils. The response time for creating an output signal from the time that the free water reaches the sponge block 14 will be about one second.

It will further be noted that the upper edges of the flanges 40 of body member 12 are beveled at 52 to mate with a similarly beveled edge 54 on the upper and inner edge of capture block 32 (see FIG. 2) so that the capture block may be readily separated when necessary from the body member 12 of the sensor by means of a fingernail or suitable tool to insert or remove the optical fiber 30 therefrom. The upper portion of the body member 12 is also provided with a pair of apertures 56 extending therethrough (FIG. 1) to permit the sensor 10 of the present invention to be securely mounted, as by screws or other fastening devices, if such should prove to be necessary.

Finally, it will be noted that the pusher bar 20 is provided with an attached, downwardly extending stem 58 which is adapted to be slidably engaged in an aperture 59 extending through the bottom wall of the body member 12 from cavity 11 thereof to the outer lower face 60 thereof, as particularly seen in FIG. 4. In the initial, unbiased position of the sensor, the lower end of the stem 58 will extend just to the lower face 60 of the sensor. However, as seen in FIG. 5, when the sweller block 14 expands downwardly (in the direction of the arrow) the stem 58 likewise projects downwardly and out of the body member 12 so as to provide a clear mechanical or visual signal that water (or other detectable liquid) has penetrated into the sensor. In the initial assemblage of the sensor (as seen in FIG. 4) the slidable fit of the stem 58 within passage 59 provides enough friction so as to hold the components of the device together in a fixed position and prevent any mechanical vibration or other shocks from disturbing the pre-set positions of the components. However, under the impetus of the expanding assembly 13 such friction fit will not be sufficient to prevent the stem 58 from being readily pushed out of the body member 12, as shown in FIG. 5, where it will remain. Even in the unlikely event that the water within the sensor 10 should evaporate and the expansible sponge block 14 dry out before the sensor is replaced, the expansible sponge block will remain in its extended (FIG. 5) position since the dried block will retain its expanded shape, and the detectable bent condition of the fiber 30 will remain. Thus, the bent-fiber optical signal as well as the visual signal provided by stem 58 remain to indicate that the sensor has been penetrated by water or other liquid and that damage to the optical connections within the splice case is possible.

While the foregoing description was particularly directed to the detection of water in a normally dry environment, such as within a fiber optic splice case, as explained previously the invention may be used to detect other liquids in wholly different environments.

Although the best mode contemplated for carrying out the present invention has been herein shown and described, it will be apparent that modifications and variations may be made without departing from what is regarded to be the subject matter of the invention.

We claim:

1. An optical fiber sensor for detecting the presence of a fluid in liquid form and for distinguishing it from its vapor phase comprising means for providing a track for receiving an optical fiber along a predetermined path with said means including a cavity to permit the fiber to be deflected out of said predetermined path, means defining a chamber spaced from said predetermined path, said chamber being provided with an opening to permit the flow of said fluid therein, a block of expansible material positioned within said chamber with said material being subject to expansion in the presence of said fluid, said chamber and block of material being relatively dimensioned so as to permit the expansion of the block of material in a particular direction within the chamber, means physically connecting said block of material to said optical fiber so that expansion of the block in said direction results in the bending of said fiber, and means for preventing said block from expanding in the presence solely of the vapor phase of said fluid but allowing expansion of the block in the presence of the liquid phase of said fluid in said chamber.

2. An optical fiber sensor according to claim 1 wherein said means for preventing comprises a restraining band secured about the periphery of the block of expansible material, the dimensions and tensile strength of said band being such that the expansive pressure of the block due to any increase in the presence of the vapor phase of the fluid in said chamber will not break the band but the expansive pressure in the block created by the presence of said fluid in liquid form in said chamber will cause the band to break permitting expansion of the block in said direction.

3. An optical fiber sensor according to claim 2 wherein said band comprises a metallic wire.

4. An optical fiber sensor according to claim 3 wherein said metallic wire is comprised of platinum.

5. An optical fiber sensor according to claim 1 including a pusher member positioned in engagement with said block of expansible material, and including a deflector element connected to said pusher element and arranged in contact with said fiber for causing said fiber to be deflected into said cavity when the block of material expands.

6. An optical fiber sensor according to claim 5 wherein said deflector element comprises a puller wire attached to said pusher bar to move therewith, said puller wire being located in engagement with said fiber so as to pull the fiber along the longitudinal axis of the fiber and cause the fiber to bend into said cavity when the block of material expands.

7. An optical fiber sensor according to claim 5 wherein said means for providing a track and said deflector element provide three spaced support surfaces of curvilinear shape for the fiber adjacent said cavity with each of such surfaces being provided with a carefully controlled geometry so that the fiber will be bent in a predetermined manner for a given length of movement of the deflector element.

8. An optical fiber sensor according to claim 1 wherein said expansible material is a compressed cellulose sponge material.

9. An optical fiber sensor according to claim 8 wherein said block of expansible material includes a pair of rigid members sandwiching said cellulose sponge material, and wherein said means for preventing comprises a restraining band secured about the periphery of the block by guide channels in said rigid members, the dimensions and tensile strength of said band being such that the expansive pressure of the cellulose sponge material due to any increase in the presence of the vapor phase of the fluid in said chamber will not break the band but the presence of said fluid in liquid form in said chamber will result in expansive pressure in the cellulose sponge material which will cause the band to break permitting expansion of the cellulose sponge material in said particular direction.

10. An optical fiber sensor according to claim 9 wherein said band comprises a metallic wire.

11. An optical fiber sensor according to claim 10 wherein said metallic wire is comprised of platinum.

12. An optical fiber sensor according to claim 1 wherein said means for providing a track includes a removable member for confining a segment of the fiber to a fixed location directly adjacent to said cavity generally permitting only sliding movement of the fiber along the longitudinal axis of the fiber as the fiber is deflected into said cavity.

13. An optical fiber sensor according to claim 1 wherein said means positioned to move with said block includes a stem positioned to move exteriorly of the sensor so as to provide a visual indicator of the presence of the liquid phase of said fluid in said chamber.

14. An optical fiber sensor for detecting the presence of free water and for distinguishing it from the presence of water vapor alone, said sensor comprising means for providing a track for receiving an optical fiber along a predetermined path with said means including a cavity to permit the fiber to be deflected out of said predetermined path, means defining a chamber, said chamber being provided with sufficient openings to freely permit the flow of water or water vapor therewithin, a block of expansible material positioned within said chamber with said material being subject to expansion in the presence of water, said chamber and block of material being relatively dimensioned so as to permit the expansion of the block of material in a particular direction within the chamber, means for causing said fiber to be deflected into said cavity when the block of material expands in the presence of water, and restraining means attached to said block of material for preventing the block from expanding in the presence of water vapor alone but permitting the expansion of the block in the presence of free water.

15. An optical fiber sensor according to claim 14 wherein said restraining means comprises a band secured about the periphery of the block of expansible material, said band being adapted to rupture under the expansive pressure of the block in the presence of free water.

16. An optical fiber sensor according to claim 15 wherein said band comprises a metallic wire.

17. An optical fiber sensor according to claim 16 wherein said metallic wire is comprised of platinum.

18. An optical fiber sensor according to claim 14 wherein said expansible material is compressed cellulose sponge material.

19. An optical fiber sensor according to claim 18 wherein said block of expansible material includes a pair of rigid members sandwiching said cellulose sponge material, and wherein said restraining means comprises a restraining band secured about the periphery of the block by guide channels in said rigid members, the dimensions and tensile strength of said band being such that the expansive pressure of the cellulose sponge material due to any increase in the presence of water vapor alone in said chamber will not break the band but the presence of free water in said chamber will result in expansive pressure in the cellulose material which will cause the band to break permitting expansion of the cellulose sponge material in said particular direction.

* * * * *